US006333030B1

(12) United States Patent
Curiel

(10) Patent No.: US 6,333,030 B1
(45) Date of Patent: Dec. 25, 2001

(54) CHIMERIC RETROVIRUS/ADENOVIRUS SYSTEM

(75) Inventor: David T. Curiel, Birmingham, AL (US)

(73) Assignee: UAB Research Foundation, Birmingham, AL (US)

(*) Notice: Subject to any disclaimer, the term of this patent is extended or adjusted under 35 U.S.C. 154(b) by 0 days.

(21) Appl. No.: 08/974,113

(22) Filed: Nov. 19, 1997

Related U.S. Application Data

(60) Provisional application No. 60/031,323, filed on Nov. 19, 1996, and provisional application No. 60/037,081, filed on Feb. 4, 1997.

(51) Int. Cl.[7] .................. A61K 48/00; C12N 15/861; C12N 15/867; C12N 15/63
(52) U.S. Cl. .................. 424/93.2; 424/93.1; 424/93.6; 435/320.1; 435/455; 435/456; 435/457
(58) Field of Search .................. 435/320.1, 455, 435/456, 457; 424/93.1, 93.2, 93.6

(56) References Cited

PUBLICATIONS

Berkner, K. L., Current Topics in Microbiology and Immunology, vol. 158, pp. 39–66.*
Kmiec, American Scientist, vol. 87, pp. 240–147, May 1999.*
Fox, Nature Biotechnology, vol. 18, pp. 143–144, Feb. 2000.*
Verma et al., Nature, vol. 389, pp. 239–242, Sep. 1997.*
Anderson, Nature, vol. 392, pp. 25–30, Apr. 1998.*
Ross et al., Human Gene Therapy, vol. 7, pp. 1781–1790, Sep. 1996.*
Reynolds et al., Molecular Medicine Today, pp. 25–31, Jan. 1999.*

* cited by examiner

*Primary Examiner*—David Guzo
(74) *Attorney, Agent, or Firm*—Benjamin Aaron Adler

(57) ABSTRACT

The present invention provides a chimeric viral vector system having a highly efficient in vivo gene delivery to cells after vascular administration and an intergrative capacity of heterologous gene sequences for stable genetic modification of cells after transduction. In this chimeric vector, an adenoviral vector is employed to deliver retroviral functions to a cell for local, in situ production of retroviral particles inside the cell by the construction of replication-defective adenoviral vectors which contain either retroviral "packaging" functions (retroviral genes gag, pol, env) and retroviral "vector" functions (retroviral LTR sequences flanking the "therapeutic" gene).

10 Claims, 13 Drawing Sheets

(4 of 13 Drawing Sheet(s) Filed in Color)

SEQUENCE LISTING

<160> NUMBER OF SEQ ID NOS: 2

<210> SEQ ID NO 1
<211> LENGTH: 29
<212> TYPE: DNA
<213> ORGANISM: artificial sequence
<220> FEATURE:
<221> NAME/KEY: primer
<223> OTHER INFORMATION: upstream primer to amplify a 133 bp PCR
      fragment containing the gag/pol transcription initiation site from
      pPAM3

<400> SEQUENCE: 1
gggaagctta tgggccagac tgttaccac                                    29

<210> SEQ ID NO 2
<211> LENGTH: 26
<212> TYPE: DNA
<213> ORGANISM: artificial sequence
<220> FEATURE:
<221> NAME/KEY: primer
<223> OTHER INFORMATION: downstream primer to amplify a 133 bp PCR
      fragment containing the gag/pol transcription initiation site from
      pPAM3

<400> SEQUENCE: 2
caaggcttcc caggtcacga tgtagg                                       26

CHIMERIC RETROVIRUS/ADENOVIRUS SYSTEM

CROSS-REFERENCE TO RELATED APPLICATION

This application claims the benefit of provisional application Nos. 60/031,323, filed Nov. 19, 1996 and 60/037,081, filed Feb. 4, 1997.

BACKGROUND OF THE INVENTION

1. Field of the Invention

The present invention relates generally to the fields of molecular biology of vectors and gene therapy. More specifically, the present invention relates to a chimeric adenoviral vector system and methods for its use.

2. Description of the Related Art

A number of gene therapy strategies for diseases of the heart, lung, and blood are based upon stable genetic modification of relevant parenchymal cells. In many contexts, this can be only achieved by direct in vivo gene delivery whereby stable transduction is achieved in situ. To this end, a variety of viral vectors have been developed to exploit their integrative capacity as a means to achieve stable genetic transduction. Vectors of this type include recombinant retroviruses and adeno-associated viruses (AAV) and have been employed in ex vivo gene transfer schemes to achieve stable genetic modification of target cells.

Despite the utility of retroviral and AAV vectors in these ex vivo contexts, employment of these vectors for direct in vivo gene delivery has been problematic. In this regard, issues of effective titer and in vivo stability have limited the utility of these vectors for the many schemes whereby direct in situ transduction of a parenchyma is required. On the other hand, recombinant adenoviral vectors can be prepared to high titer, and possess in vivo stability, both factors which have allowed their employment for direct in vivo gene delivery to differentiated target cells. The limitation of adenoviral vectors, however, is that the derived heterologous gene expression is only transient. This is based, in part, upon the fact that adenoviral vector transduced cells are immunologically eradicated by the host. In addition, the parent adenovirus lacks the capacity to integrate its genome in the host chromosome.

The prior art is deficient in the lack of effective vector system which allows stable genetic modification of cells after direct in vivo vector administration. The present invention fulfills this longstanding need and desire in the art.

SUMMARY OF THE INVENTION

Retroviral integrative functions can be exploited, in the context of adenoviral vectors, to derive a system which can achieve efficient, stable transduction of target cells in vivo. The present invention shows that retroviral vector packaging and retroviral vector functions can operate in the context of adenoviral vector constructs, with the successful derivation of integrative progeny retroviral vectors. In this schema, target cells are induced to function as transient retroviral "producer cells" by a combination of adenoviral vector-mediated delivery of retroviral vector sequences in concert with adenoviral vector expression of retroviral packaging function. In the in vivo context, high efficiency delivery of retroviral packaging and vector functions could be achieved at parenchymal sites via adenoviral vectors to achieve this in situ.

Thus, locally elaborated retroviral vectors could secondarily infect neighbor cells to achieve stable genetic transduction. Thus, a "chimeric" vector system has been developed which exploits favorable characteristics of each component vector.

It is an object of the present invention to develop adenoviral vectors containing retroviral integrative functions and to optimize their employment in vitro, for achievement of stable transduction of target cells.

It is another object of the present invention to employ these chimeric vectors to achieve stable in vivo genetic modification of parenchymal cells relevant to diseases of the heart, lung, and blood.

The development of adenoviral vectors with integrative capacity would allow these vectors to achieve stable integration of transgenes in vivo. This strategy would thus exploit the favorable characteristics of each component vector system to allow stable gene expresssion at parenchymal target sites significantly improving the possibilities of achieving effective genetic correction in the context of gene therapy applications for diseases of the heart, lung, and blood.

In one embodiment of the present invention, there is provided a chimeric adenoviral/retroviral vector, comprising: at least one adenoviral vector containing retroviral sequences.

In one embodiment of the present invention, there is provided method of stably transducing target cells, comprising the step of administering the chimeric adenoviral/retroviral vector of the present invention to an individual in need of such treatment.

Other and further aspects, features, and advantages of the present invention will be apparent from the following description of the presently preferred embodiments of the invention given for the purpose of disclosure.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 6 (Parts A–B) shows the persistant gene expression. Target cells were infected with AdLNCMVGFP plus AdCMVAmpg or AdLNCMVGFP alone and analyzed for stable genetic transduction.

(FIG. 9 A) Hematoxylin-stained section taken from a two virus, subcutaneous nodule. SKOV3$_{ip1}$ cells were implanted intraperitoneally and animals challenged with either AdLNCMVGFP alone (FIG. 9E) or AdLNCMVGFP plus AdCMVAmgp (FIG. 9F). Analysis was by fluorescent microscopy for expression of the GFP reported at day sixteen.

DETAILED DESCRIPTION OF THE INVENTION

Figure 1:
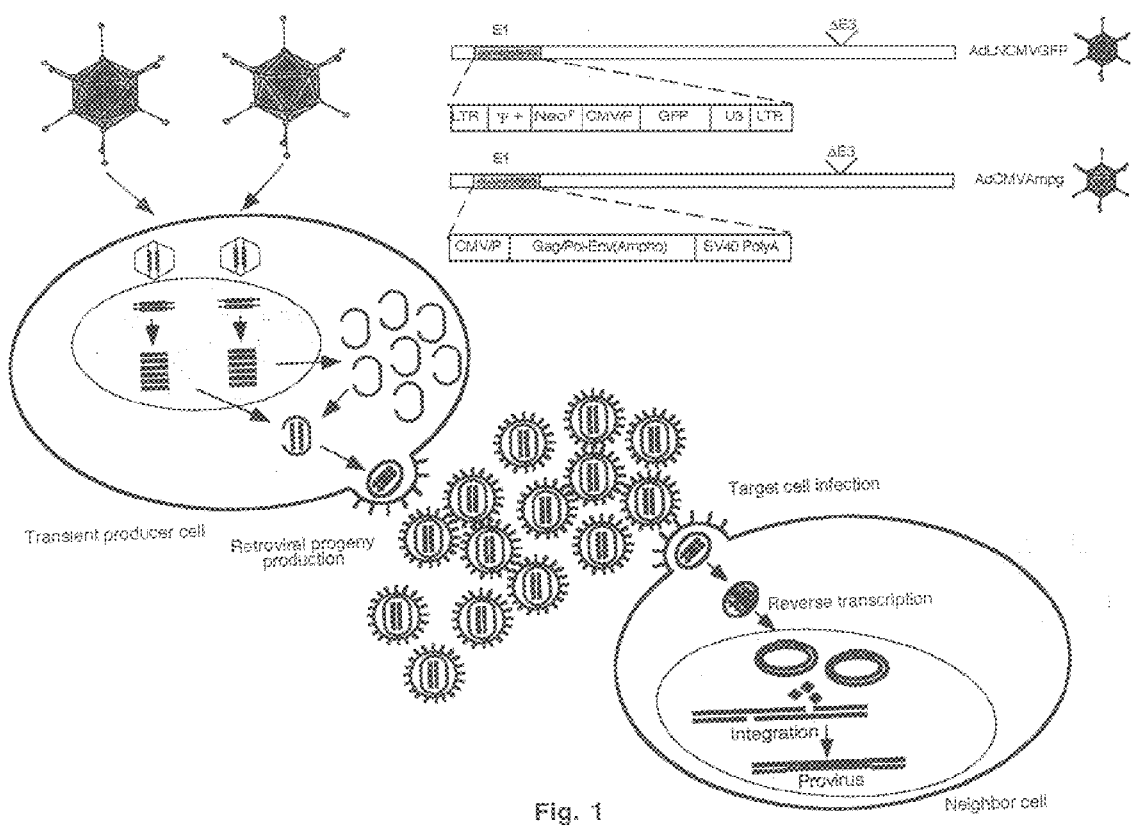
FIG. 1 shows the schema of local generation of retroviral vector at a target organ site. Adenoviral vectors encoding retroviral vector and packaging functions accomplish in vivo gene transfer to target parenchymal cells at high efficiency, rendering them transient retroviral producer cells. The locally elaborated retroviral particles can thus directly infect neighbor cells.

The present invention is directed to a vector system that provides both highly efficient in vivo gene delivery to cells after vascular administration and has an integrative capacity of heterologous gene sequences to accomplish stable genetic modification of cells after transduction. In the chimeric vector of the present invention, an adenoviral vector is employed to deliver retroviral functions to a cell for local, in situ production of retroviral particles inside the cell. This is accomplished by the construction of replication-defective adenoviral vectors which contain either retroviral "packaging" functions (retroviral genes gag, pol, env) and retroviral "vector" functions (retroviral LTR sequences flanking the "therapeutic" gene). These adenoviral vectors are capable of co-delivering gene products with high efficiency to cells based on the adenoviral vector's recognized capacity to achieve efficient in vivo transduction after vascular vector administration.

Cells, such as hepatocytes tranduced with these adenoviral vectors are then rendered into transient retroviral vector "producer cells". These cells transiently express retroviral vector functions. The cells can thus elaborate retroviral particles containing the therapeutic gene. By virtue of the "local", in situ production of retroviral particles, efficient transduction of neighboring cells is achieved with the elaborated retroviral particles. This method thus overcomes the obligate loss of retroviral vectors which occurs with "distant" vascular administrations. In addition, transduced "neighbor" cells are stably modified by virtue of the fact that retroviral vectors accomplish the transduction event. This event thus overcomes the principal limitation of adenoviral vectors by allowing for an integrative transduction event.

One unique attribute of this chimeric viral vector system is thus the exploitation of adenoviral vector delivery elements to achieve effective in situ retroviral transduction. This concept can be extended to deliver other genes which could render cells further susceptible to retroviral vectors produced "locally". In this regard, retroviral infection is enhanced by proliferation of target cells.

The present invention is directed to a chimeric adenoviral/retroviral vector, comprising: at least one adenoviral vector containing retroviral sequences. Preferably, the chimeric adenoviral/retroviral vector comprises: (a) a replication-deficient adenoviral vector containing retroviral vector functions; and (b) at least one replication-deficient adenoviral vector containing retroviral packaging functions. Preferably, the retroviral vector functions comprise a heterologous gene and such gene is flanked by retroviral long terminal repeats. Generally, the retroviral packaging functions are selected from the group consisting of gag, pol and env, or combinations thereof. A person having ordinary skill in this art would recognize that one may substitute alternate env genes to more specifically target a cell. For example, one may use the env gene is a vesicular stomatitis virus G-glycoprotein as described in detail below. Preferably, the heterologous gene is selected from the group consisting of a gene encoding a therapeutic protein, a selectible marker and a reporter gene. A person having ordinary skill in this art would recognize that one may exploit a wide variety of genes encoding proteins, e.g., therapeutic proteins, either to replace such a protein or to augment or inhibit a specific biochemical activity.

The present invention is also directed to a method of stably transducing target cells, comprising the step of administering the chimeric adenoviral/retroviral vector of the present invention to an individual in need of such treatment. Preferably, the chimeric adenoviral/retroviral vector comprises: (a) a replication-deficient adenoviral vector containing retroviral vector functions; and (b) at least one replication-deficient adenoviral vector containing retroviral packaging functions. Preferably, the retroviral vector functions comprise a heterologous gene and such gene is flanked by retroviral long terminal repeats. Generally, the retroviral packaging functions are selected from the group consisting of gag, pol and env, or combinations thereof. A person having ordinary skill in this art would recognize that one may substitute alternate env genes to more specifically target a cell. For example, one may use the env gene is a vesicular stomatitis virus G-glycoprotein as described in detail below.

Preferably, the heterologous gene is selected from the group consisting of a gene encoding a therapeutic protein, a selectible marker and a reporter gene. A person having ordinary skill in this art would recognize that one may exploit a wide variety of genes encoding proteins, e.g., therapeutic proteins, either to replace such a protein or to augment or inhibit a specific biochemical activity. Using the methods described below, one may administer a replication-deficient adenoviral vector containing retroviral vector functions; and said replication-deficient adenoviral vector containing retroviral packaging functions are co-transduced into a host cell, wherein expression of the genes encoded by said adenovirus shuttle vector results in the production of retrovirus particles containing said therapeutic gene, wherein said retrovirus particles infect neighboring cells, wherein said retrovirus particles stably integrate said therapeutic gene into said host cells' genomic DNA.

A person having ordinary skill in this art would recognize that one may specifically target the chimeric adenoviral/retroviral vector of the present invention by various manipulations. For example, one may genetically modify the fiber or knob component of the adenoviral vector, e.g., by incorporating a ligand that specifically recognizes a cell surface receptor. Alternatively, one may target the adenovirus immunologically using single chain antibodies of Fab fragments as is known in the art.

The following examples are given for the purpose of illustrating various embodiments of the invention and are not meant to limit the present invention in any fashion.

EXAMPLE 1

Employment of Adenoviral Vectors Containing Retroviral Integrative Functions for Stable Transduction of Target Cells To achieve long term heterologous gene expression consequent to efficient in vivo gene delivery, retroviral integrative features can be coupled to adenoviral vector systems. This is accomplished by employing replicative-deficient adenoviral vectors to deliver both retroviral packaging functions and retroviral vector sequences to target cells in situ. The co-transduced cells then function as retroviral producer cells. In this schema, the locally elaborated retroviral particles stably transduce "neighbor cells" within the surrounding parenchyma, thus achieving efficient integration of transgene sequences of relevant target organs for gene therapy purposes. The ability of adenoviral vectors to deliver relevant retroviral functions for the efficient induction of target cells to function as retroviral producer cells is shown.

EXAMPLE 2

Plasmid Vectors and Cells

To generate the adenoviral/retroviral chimeras, individual elements of the retroviral genome components were first incorporated into two distinct adenoviral shuttle vectors designated pCAAmpg and pΔE1LNCX. Shuttle vectors were also generated containing reporter genes, resulting in pΔE1LNCMVGFP which encodes the green fluorescent protein (GFP) cDNA and pΔE1LNCMVLacZ encoding the *Escherichia coli* β-galactosidase (LacZ) gene.

For pCAAmpg, the DNA fragments encoding the retroviral gag/pol and amphotropic env genes were isolated from pPAM3 (provided by Dr. Dusty A. Miller, Fred Hutchinson Cancer Research Center, Seattle, Wash.) in a two-step PCR/restriction digest procedure as follows: A 133 bp PCR fragment including the gag/pol transcription initiation site was amplified from pPAM3 using an upstream primer, 5'-gggaagcttatgggccagactgttaccac (SEQ ID No. 1), containing a HindIII site, and a downstream primer 5'-caaggcttcccaggtcacgatgtagg (SEQ ID No:2), encompassing an internal PstI site. This fragment was digested with HindIII and PstI prior to cloning. The remaining 7.0 kb gag/pol/env segment was obtained from pPAM3 with PstI-HpaI digestion. The two retroviral fragments were triple ligated into the adenoviral shuttle vector pCA13 (Microbix Biosystems Inc., Ontario, Canada) at HindIII-EcoRV sites to obtain the pCAAmpg vector (13.9 kb).

To construct an adenoviral shuttle vector containing retroviral integration sequences, neomycin resistance cDNA, a CMV promoter and multiple cloning sites, the retroviral vector pLNCX (Dr. A. Dusty Miller) was partially digested with EcoRI and HindIII to obtain a 3.6 kb fragment. This fragment was subsequently subcloned into a modified version of pZero-1™ (Invitrogen, La Jolla, Calif., USA) in which a ClaI site was introduced by silent mutation between the EcoRV and NotI sites. The resultant construct was labeled as pEH3.6. The remaining retroviral vector sequence was obtained by ApaI and HindIII digestion and the resulting fragment was subcloned into p-Zero-1™ at HindIII and EcoRV sites to be pHA0.9. The 3.6 kb ClaI-HindIII fragment from pEH3.6 and the 1.0 kb HindIII-XhoI fragment from pHA 0.9 were triple ligated in pΔE1SP1A (Microbix, Biosystems Inc.) at ClaI and XhoI sites to create pΔE1LNCX. The 0.9 kb GFP cDNA segment was excised from pEGFP-NI (Clontech Inc., Palo Alto, Calif., USA) by HindIII-HpaI digestion and subcloned into pΔE1LNCX at HindIII and HpaI sites. A similar scheme was used to construct pΔE1LNCMVLacZ from pΔE1LNCX. The shuttle vectors pCAAmpg, pΔE1LNCX, pΔE1LNCMVGFP, pΔE1LNCMVLacZ were confirmed by restriction enzyme analysis and partially sequenced using USB 70770 Sequencing kit (Amersham, Cleveland, Ohio, USA).

NIH-3T3 fibroblasts, 293 cells, EJ bladder carcinoma cells (ATCC, Rockville, Md.), W162 (Gary Ketner, Princeton University) and SKOV3$_{ip1}$ cells (Dr. Janet Price, M.D. Anderson Cancer Center, Houston, Tex.) were maintained in complete medium composed of Dulbecco's Modified Eagle's Medium/Ham's F12 (DMEM/F12, Mediatech, Inc.; Washington, D.C.) supplemented with 10% fetal bovine serum (FBS, Hyclone; Logan, Utah), 2 mM glutamine (Mediatech) and penicillin/streptomycin (Cellgro Mediatech). All cells were maintained at 37° C. in 5% $CO_2$.

EXAMPLE 3

Generation of Recombinant Adenoviral Vectors

E1A/B and E3 deleted replication-deficient recombinant adenoviral vectors were generated by in vitro homologous recombination method. In these studies, the pCAAmpg, pΔE1LNCMVLacZ or pΔE1LNCMVGFP shuttle plasmids were co-transfected with pBGH11 (Microbix Biosystems Inc.) into 293 cells to generate AdCMVAmpg, AdLNCMVLacZ or AdLNCMVGFP, respectively. Each adenovirus was passed through three rounds of plaque purification and subsequently confirmed by PCR analysis and restriction enzyme mapping. Recombinant adenoviruses were propagated on the permissive 293 cell line, purified twice by CsCl gradient centrifugation, and plaque titered using standard methods.

EXAMPLE 4

Retroviral Particle Generation and Detection

Cells were plated into 100-mm tissue culture plates ($10^6$ cells/plate) in complete medium containing 10% FBS and incubated overnight at 37° C. in 5% $CO_2$. For initial testing of plasmid constructs, 293 cells were transfected by calcuim phosphate precipitation with either pΔE1LNCMVLacZ plus pCAAmpg or with pLNCLX ane pPAM3. The following day, the cells were fed with fresh complete medium. At 48 h post-transfection, the supernatant was harvested and used to determine retroviral titer on NIH-3T3 cells. For adenoviral infection, the culture medium was aspirated and replaced with DMEM/F12 plus 2% FBS containing either AdCM-VAmpg plus AdLNCMVGFP, or AdLNCMVGFP alone, at a ratio of 50 plaque-forming units (pfu)/cell for each group. After 3 hours of incubation, the medium was aspirated and the cells were rinsed several times with PBS and fed with complete medium. Retrovirus production was determined either directly by titering the supernatant 48 h post-infection, or indirectly by monitoring neighbor cells for retroviral infection. Long term cultures for stable integration were passed at 8 day intervals. Retroviral titer was carried out on NIH-3T3 cells. For this analysis, culture supernatant from retroviral producer cells was harvested, filtered (0.45 µm), and added to recipient cells at a 1:1 ratio to complete medium plus 10 mg/ml polybrene. After 48 h, cells expressing LacZ were visualized by X-gal histochemistry and titer was determined by quantitation of the total blue cells/dish. Titer was expressed as infectious virions/ml.

EXAMPLE 5

LacZ, GFP, and Replication-competent Retrovirus (RCR) Assay

Cellular expession of LacZ was quantitatively analyzed by staining with X-gal (5-bromo-4-cholor-3-indlyl-β-D-galactoside). Cells were fixed with 0.25% glutaraldehyde/0.1 M sodium phosphate for 15 minutes at room temperature followed by washing with PBS and incubation overnight with X-gal staining solution (0.2% X-gal/2 mM $MgCl_2$/4 mM $K_4Fe(CN)_6$/4 mM $K_4Fe(CN)_6 3H_2O$ in PBS) at room temperature. X-gal positive (blue) cells were counted under light microscopy. Cellular GFP expression was quantitatively analyzed by FACS analysis, and by visualization using fluorescent microscopy according to the manufacturer's protocol. (Clontech, Calif., USA).

Feline $S^+L^-$ (PG-4) cells were seeded in McCoy's 5A medium (BioWhattaker, Walkersville, Md.) plus 15% FBS into 60-mm culture dishes approximately 24 h prior to inoculation. Five replicate dishes were inoculated with 0.2 ml of sample dilutions; 1 and 10 focus forming units of amphotropic murine retrovirus 4070A as a positive control; and culture medium to serve as a negative control After a 2 h adsorption period at 36±2° C. and fed with fresh medium, as necessary, for a period of 4–5 days until foci of transformed cells were fully developed in the positive control dishes. The dishes were examined microscopically, and foci were counted. The assay was considered to be valid if no foci were observed in the negative control and the positive control dilutions had a mean titer within one log of the validated mean titer of the positive control virus lot.

EXAMPLE 6

In Vivo Experiments and Provirus Integration

Female nude mice (4 to 6 weeks old) were injected i.p. with $1 \times 10^7$ $SKOV3_{ip1}$ cells. Five days later, animals were i.p. injected with either AdCMVAmpg plus AdLNCMVGFP, or AdLNCMVGFP alone ($1 \times 10^9$ pfu per mouse for each virus). Animals were sacrificed at 16 days post-adenovirus challenge. Tumor nodules were harvested, fixed in 4% paraformaldehyde/PBS, sectioned and analyzed by fluorescence microscopy. For subcutaneous mixing studies, $SKOV3_{ip1}$ cells were infected ex vivo at 50 pfu/per cell. Sixteen hours post-infection, the cells were washed twice with PBS, trypsinized, harvested, counted, and mixed at a ratio of 1:4 with non-infected $SKOV3_{ip1}$ cells. A total of $5 \times 10^6$ mixed cells were injected subcutaneously into the flanks of nuce mice. Animals were sacrificed at day 20 post-injection. Tumor nodules were harvested for analysis by fluorescence microscopy.

To detect provirus integration, the high molecular weight fraction DNA was extracted from adenovirus treated cells. The DNA was MunI digested, resolved on a 0.8% agarose gel, and probed with a $^{32}$P-labeled 1.4 kb fragment containing a retroviral vector sequence, which was obtained by PCR amplifying of AdLNCMVGFP from 4.8 kb to 6.2 kb. DNA labeling, membrane transfer, hybridization and washing procedures were performed according to the manufacturer's protocol (Amersham).

EXAMPLE 7

Elaboration of Retroviral Particles at Parenchymal Target Sites to Achieve Stable Transduction of Neighbor Cells The present invention developed a "composite" vector system that combines the high efficiency in vivo gene delivery characteristics of recombinant adenoviral vectors with integrative capacities derived from retroviruses. This is accomplished by rendering adenoviral vector infected target cells into transient "retroviral producer cells" via adenoviral vector-mediated delivery of retroviral packaging functions and retroviral vector sequences. In this manner, the locally elaborated retroviral vectors can infect neighboring parenchymal cells via an integrative vector. The conceptual basis of this approach in depicted in FIG. 1.

Figure 2A:
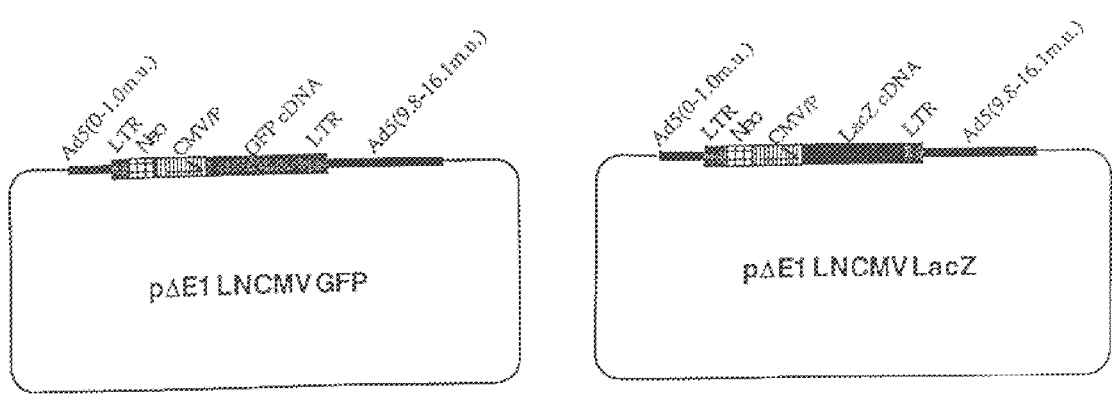
FIG. 2 (Parts A–B) shows (FIG. 2A) Maps of adenoviral shuttle plasmids containing retroviral packaging functions, and (FIG. 2B) Maps of adenoviral shuttle plasmids containing retroviral vector functions.
Figure 2B:
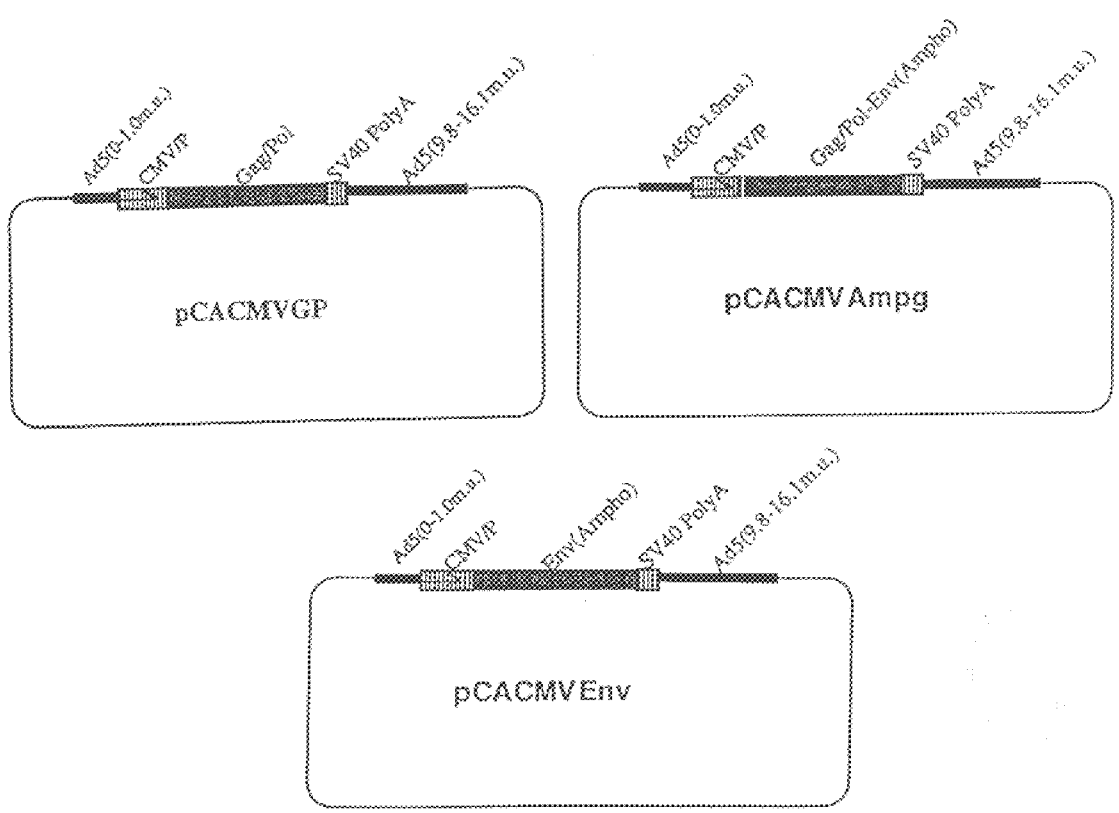
Figure 3A:
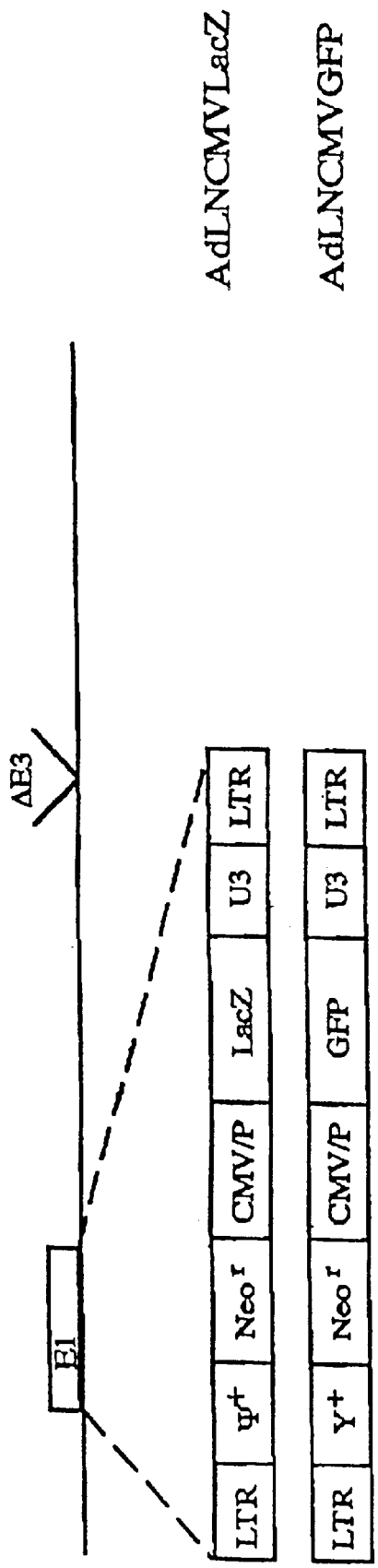
FIG. 3 shows the structural validation of adenoviral vector via molecular analysis for E1 substitution recombinant adenovirus encoding Moloney murine Leukemia retrovirus vector components and gene interested expression cassette (FIG. 3A) and E1 substitution recombinant adenovirus expressing retroviral packaging components (FIG. 3B).
Figure 3B:
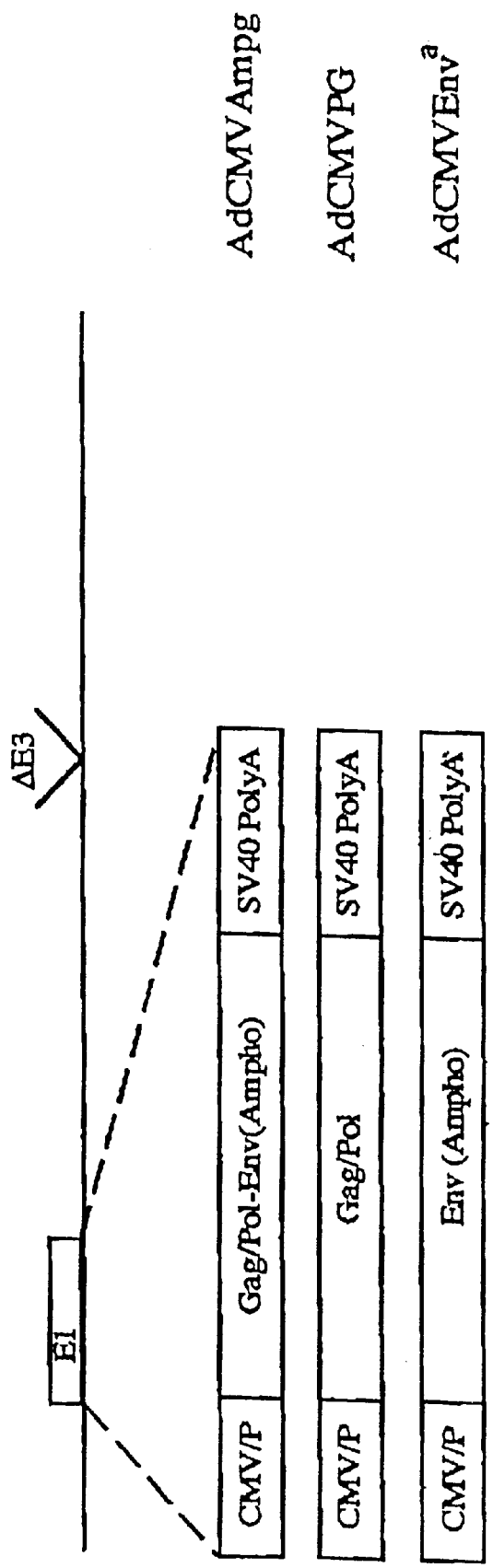

As a first step towards implementing this strategy, adenoviral vectors encoding retroviral vector sequences and retroviral packaging functions were derived. The derivation of these adenoviral vectors is based on methods whereby an adenoviral "shuttle" vector containing the transgene is co-transfected with the adenoviral packaging plasmid pJM17. The recombination of homologous regions within these plasmids results in a replication-deficient, E1A/B-deleted, adenoviral vector. As the adenoviral shuttle plasmids contain the intact expression cassettes destined for adenoviral vector incorporation, they provide the means to validate the functional utility of the transgene sequences a priori. Based on this concept, a series of adenoviral shuttle vector plasmids containing relevant retroviral transgene sequences were derived. Thus, a series of plasmids were derived with retroviral functions gag/pol/env, gag/pol, or env cloned into the polylinker of the adenoviral shuttle vector pCA13 (FIG. 2).

These vectors would thus allow expression of the indicated retroviral packaging functions via a CMV intermediate/early enhancer-promoter. In addition, adenoviral shuttle plasmids encoding retroviral vector sequences were derived. In this instance, the predicted adenoviral vector would function as a high efficiency delivery vehicle of the encoded transgene sequences. These retroviral vector sequences would then be packaged into retroviral particles, a process for which vector expression in target cells is not required. Thus, in these instances retroviral vector sequences encoding either a E. coli β-galactosidase (LacZ) gene, in conjunction with a neomycin selectable marker, or the reporter gene green fluorescent protein (GFP) also in conjunction with a neomycin selectable marker, were cloned into polylinker of the "promoterless" adenoviral shuttle vector (FIG. 2).

These retrovirus vector gene constructs contain the indicated marker/reporter sequences flanked by intact retroviral long terminal respects (LTRs). This was accomplished as these functions are the minimal sequences required in cis to allow retroviral vector integration. These plasmids were all confirmed after construction by indirect analysis with restriction endonuclease digestion and direct analysis by dideoxy chain termination sequencing.

Functional analysis was used to confirm the operation of retroviral packaging functions in the context of the adenoviral shuttle plasmid. For this study, the utility of the adenovirus shuttle plasmid containing retroviral packaging functions (pCAAmpg) was compared to the utility of a standard packaging plasmid, pPAM3, which contains the ecotropic retroviral genes gag/pol/env under the control of Moloney Leukemia Virus (MLV) LTR. These plasmids were analyzed for their ability to rescue retroviral vector sequences from the control retroviral vector plasmid pLNCLZ, which contains a retroviral vector cassette whereby the LacZ reporter gene is flanked by retroviral LTRs. After co-transfection of the plasmids into 293 cells, supernatants were harvested and used to infect the murine fibroblast cell line NIH-3T3 by standard methods. The cells were then visualized 48 hours after infection after staining for the LacZ product with X-gal immunohistochemistry.

Functional validation of adenoviral shuttle plasmids containing retroviral packaging functions showed that 293 cells were transduced with indicated plasmids by $CaPO_4$ and supernatants used to infect target NIH-3T3 cells with X-gal staining at 48 h for the product of the LacZ gene. Transfections were with: a) pPAM3 and pLNCLZ; b) pPAM3; c) pLNCLZ; and d) pCAAmpg and pLNCLZ. The transfection with pPAM3 and pLNCLZ was positive. The transfection with pPAM3 and pLNCLZ was negative. The transfection with pCAAmpg and pLNCLZ was positive.

Co-transfection of the control plasmids pPAM3 and pLN-CRZ yielded retroviral transducing particles, as indicated by the presence of LacZ positive NIH-3T3 cells. In contrast, transfection with either of these plasmids alone did not yield transducing retroviral particles. Next, co-transduction of the adenoviral shuttle vector encoding the retroviral packaging functions (pCAAmpg) with the retroviral vector plasmid pLNCLZ was then carried out. As for the co-transfection with both of the control plasmids (pPAM3 and pLNCLZ), LacZ transducing retroviral particles were derived in this analysis. Thus, retroviral packaging functions are exploitable for retroviral particle derivation in the context of an adenoviral shuttle plasmid.

Studies were directed at determining whether retroviral vector sequences could be rescued from an adenoviral shuttle plasmid. For this analysis, retrovirus particles were derived and transducing particles were analyzed as described above. The packaging plasmid employed for this analysis was pPAM3. It was utilized to rescue retroviral particles either from a conventional retroviral vector plasmid, pLNCLZ, containing a LacZ gene flanked by retroviral LTRs, or from an adenoviral shuttle plasmid containing the same LTR-neo-CMV-LacZ-LTR segment (pΔE1LNCMVLacZ). As before, co-transfection of 293 with pPAM3 and pLNCLZ generated LacZ transducing retroviral particles, as indicated by X-gal staining of NIH-3T3 indicator cells. Additionally, neither plasmid alone possessed this capacity. Importantly, co-transfection of the adenoviral shuttle plasmid containing the retroviral vector sequence, pΔE1LNCMVLacZ, with the control retroviral packaging plasmid, pPAM3, also could be shown to generate LacZ transducing retroviral particles.

Functional validation of adenoviral shuttle plasmids containing retroviral vector functions was performed. For this analysis, 293 cells were transfected with indicated plasmids by $CaPO4$ and supernatants used to infect target NIH-3T3 cells with X-gal staining at 48 h for the product of the LacZ gene. Transfections were with: a) pPAM3 and pLNCLZ; b) pPAM3; c) pLNCLZ; and d) pPAM3 and pΔE1LNCMVLacZ. The transfections were with pPAM3 and pLNCLZ was positive; the transfection with pPAM3 was negative; the transfection with pLNCLZ was negative; and the transfection with pPAM3 and pΔE1LNCMVLacZ was positive. Thus, retroviral vectors can be rescued from adenoviral shuttle plasmids for derivation of transducing particles.

These studies have thus independently established that retroviral packaging and vector functions can operate in the context of adenoviral shuttle plasmids to allow the generation of in vivo retroviral particles. It was important to demonstrate that these functions, when both in an adenoviral shuttle plasmid context, could also function to yield retroviral particles. For this analysis, the ability of retroviral packaging functions were evaluated in an adenoviral shuttle vector, pCAAmpg, to rescue retroviral vector functions in the adenoviral shuttle vector plasmid, pΔE1LNCMVLacZ. Control experiments with pPAM3 and pLNCLZ established the ability to derive particles in this assay. In addition, control transfection with pCAAmpg or pΔE1LNCMVLacZ also failed to yield particles independently. Co-transfection of these two plasmids, however, yielded LacZ transducing retroviral particles, as was noted in the positive control study.

The functional validation of adenoviral shuttle plasmids containing retroviral vector functions was performed. Transfection and supernatant assay was as described above. Transfections were with: a) pPAM3 and pLNCLZ; b) pCAAmpg; c) pΔE1LNCMVLacZ; and d) pCAAmpg and pΔE1LNCMVLacZ. Transfection with pPAM3 and pLNCLZ were positive; the transfection with pCAAmpg was negative; the transfection with pΔE1LNCMVLacZ was negative; and the transfection with pCAAmpg and pΔE1LNCMVLacZ was positive. Thus, this experiment confirms the generation of retroviral particles from adenoviral shuttle plasmids containing the minimum requisite retrovirus functions. This finding thus establishes the rationale to derive adenoviral vectors constructed on this basis.

Figure 4:
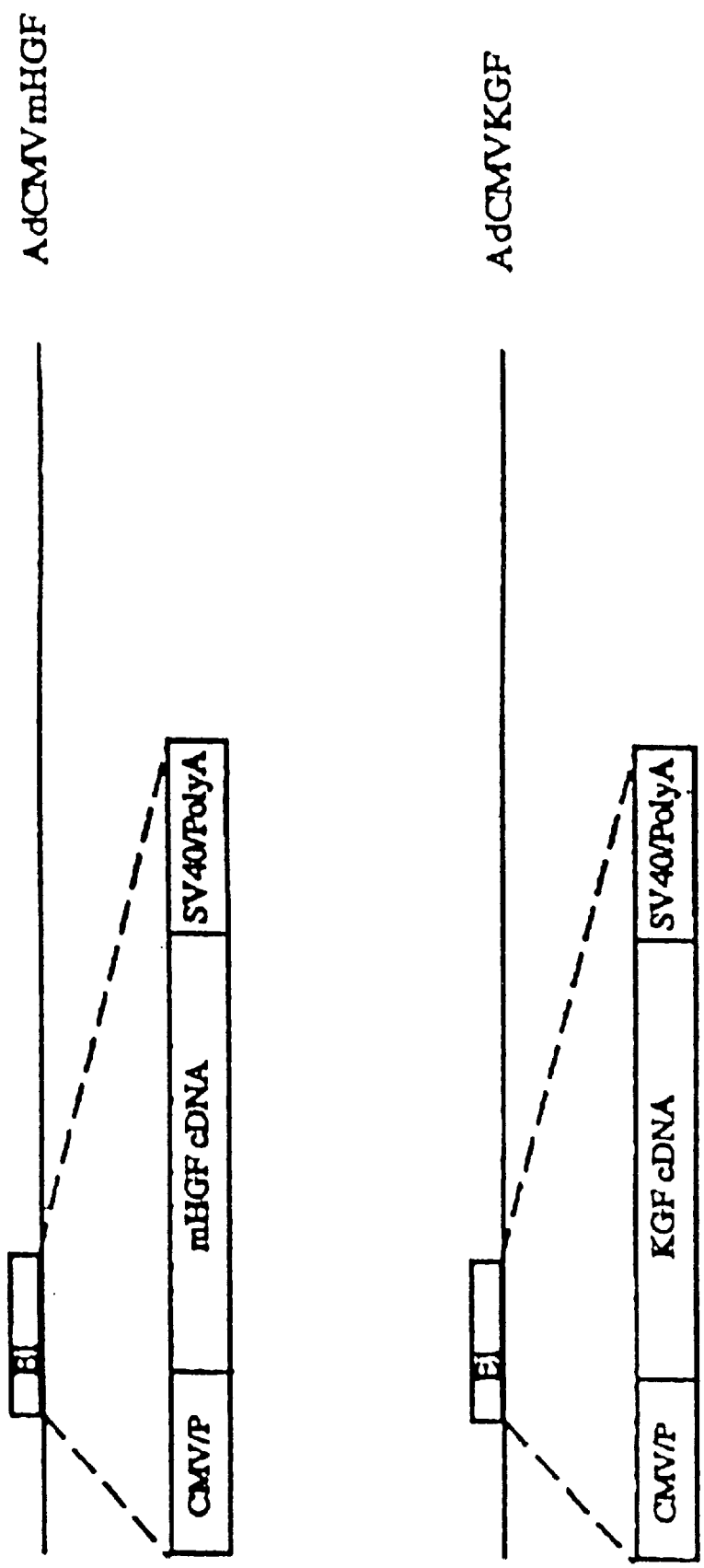
FIG. 4 shows maps of constructed adenoviral vectors encoding HGF and KGF for induction of target cell proliferation in vivo.

Based on these results, adenoviral vectors were constructed encoding retroviral packaging functions or retroviral vector functions. These vectors were generated by standard methods via co-transfection of the indicated shuttle plasmids with the adenoviral packaging plasmid pJM17 as previously described. Isolated plaques were then expanded, confirmed for identity by polymerase chain reaction (PCR), and plaque purified by three serial passages. After expansion, the identity of the vectors was confirmed by restrictive endonuclease digestion and PCR analysis of heterologous DNA segments at the E1A region at the adenoviral genome. An example of this conformation is shown in FIG. 4. These vectors are all E1A/B-deleted, replication-incompetent adenoviral vectors. These vectors were characterized in vitro for the functional utility of their retroviral packaging and vector functions as done for the corresponding shuttle plasmids. The demonstration of the functional utility of these retroviral segments in the context of adenoviral vector allows execution of in vivo studies.

Based on these concepts, the present invention discloses a strategy in which adenoviral vectors are employed to deliver growth factors to the relevant target parenchyma to induce proliferation. This maneuver can be employed in conjunction with in situ generation of retroviral vector via adenoviral-mediated gene delivery of retroviral vector and/or packaging functions. In this method, adenoviruses achieve high efficiencies of in vivo gene delivery to target parenchyma of relevant growth factor genes. The high efficiency of delivery at relevant sites allows high local concentrations of the growth factors to be achieved, with enhanced induction of target cell proliferation.

The adenoviral/retroviral chimeric vectors has been configured and its function validated. The recombinant adenovirus containing the retroviral vector sequences, AdLNCMVLacZ, has been constructed and functionally validated. A strategy was derived to achieve high, transient transfection of a non-293 cell line with retroviral packaging functions to determine whether retroviral vector sequences could be rescued from the context of an adenoviral genome. For this requirement, the adenovirus-polylysine vector (AdpL) was employed. For this study, HeLa cells were transfected with AdpL complexes containing the plasmid pPAM3 to provide expression of retroviral packaging functions, and then infected with AdLNCMVLacZ. Control experiments demonstrated that co-transduction of HeLa with pPAM3 and PLNCLZ via AdpL resulted in the production of retroviral particles. In contrast, AdpL-transfection of the plasmid PLNCLZ only did not. When AdpL transfection with pPAM3 was followed by infection with AdLNCMVLacZ, LacZ transducing retroviral particles could be obtained. Of note, when HeLa cells were not pre-treated with AdpL/pPAM3, no such retroviral particles could be obtained. Thus, "carry-over" of the LacZ encoding adenovirus from the producer cells to the target cells did not explain this result. Thus, retroviral vector sequences can be rescued from adenoviral vectors with the successful derivation of transducing retroviral particles.

Functional validation of AdLNCMVLacZ was performed. For this analysis, HeLa cells were transfected via the AdpL method with retroviral packaging and/or vector plasmids. In some instances cells were then infected with AdLNCMV-LacZ. Supernatants was then harvested and analyzed for LacZ transducing retroviral particles, as before. Transduction/infection conditions were: a) AdpL transfection with pPAM3 and PLNCLZ, b) AdpL transfection with PLNCLZ, c) AdpL transfection with pPAM3 followed by infection with AdLNCMVLacZ, d) Ad infection with AdLNCMVLacZ only. Transduction/infection with AdpL transfection with pPAM3 and PLNCLZ was positive; AdpL transfection with PLNCLZ was negative; AdpL transfection with pPAM3 followed by infection with AdLNCMVLacZ was positive; and Ad infection with AdLNCMVLacZ only was negative. All vectors used for these studies are E1 A/B-deleted, replication-incompetent adenoviral vectors.

EXAMPLE 8

Patterns of Gene Expression in Retroviral Producer Cells Induced Via Adenoviral Vector-mediated Delivery The basis of this strategy is efficient expression in target cells of retroviral packaging functions to allow rescue of retroviral vector sequences from the adenovirus vector vehicles. The patterns of gene expression of the retroviral packaging functions gag/pol/env were evaluated in various "conventional" packaging systems, and compared to the pattern achieved by the adenoviral vector AdCMVAmpg, which also encodes these functions. In this regard, the packaging cell line GP+Am12 has been stably transduced to express amphotrophic retroviral functions and has been validated as an efficient vehicle for packaging of retroviral vectors. In addition, transient transfection of the human embryonic kidney cell 293 via $CaPO_4$ microcrystalline particles with the kat packaging plasmids pKat2ampac and pLNCLZ has been shown to efficiently package co-transduced retroviral vector plasmids. These two cellular systems were compared to HeLa cells transduced with the adenoviral vector AdCMVAmpg, with analysis of the magnitude and pattern of packaging functions achieved.

For this analysis, the packaging cell line GP+Am12, 293 cells transduced via $CaPO_4$ with the plasmid pKat2ampac, and HeLa cells infected with adenoviral vector AdCM-VAmpg are subject to Northern blot analyses at various time points after induction. Comparable amounts of extracted total cellular RNA are transferred on nitrocellulose membranes and the resulting blots probed with $^{32}$P-labeled oligonucleotides corresponding to the retrovirus gag, pol, or env genes. The resulting blots provide a comparison of the magnitude and pattern of retroviral packaging gene functions achieved via adenoviral delivery compared to levels achieved via conventional packaging technologies. This data allows one to optimize retroviral vector production from transient transfection of target cells via adenoviral vehicles.

EXAMPLE 9

Production of Retroviral Vectors Via Transient Producer Cells Induced with Adenoviral Vector-mediated Gene Transfer After establishing that an appropriate level and pattern of retroviral packaging functions may derive from an adenoviral vector encoding the retroviral genes gag/pol/env, the production of transducing retroviral particles was accomplished. Comparison is made to "conventional" retroviral packaging systems including stable retroviral producer cell lines established by transduction of the amphotropic retroviral producer line GP+Am12 with the plasmid pLNCLZ. This line stably produces retroviral particles encoding LacZ/neomycin. In addition, retroviral vectors were generated via transient co-trangfection of 293 cells with CaPO4 procedures with the amphotropic retroviral packaging plasmid pPAM3 in combination with the retroviral vector plasmid pLNCLZ. For comparison, HeLa cells were co-transduced with normalized amounts of adenoviral vectors encoding retroviral packaging functions (AdCMVmpg) or retroviral vector functions (AdLNCMVLacZ).

At 48 h post-induction, supernatants were harvested from target cells and analyzed for content of produced retroviral particles. A number of analyses were utilized to determine the titer and function of produced retroviral vectors. The magnitude of produced particles was directly determined by Northern blot for analysis of supernatants with probe via a cDNA for the retroviral vector sequences. Serial dilutions of each supernatant were compared to standards containing known amounts of the retroviral vector plasmid. This assay thus yields information as to the level of retroviral vector sequences packaged into produced retroviral particles with each packaging system. In addition, the titer of the produced retrovirus vector were directly determined by two methods. First, supernatants were delivered to the indicator cell line NIH-3T3 with infection by standard methods. After 48 h, these cells were stained for the product of the LacZ gene with FDG and analyzed by FACS for transduction frequency. In addition, similarly infected NIH-3T3 cells were subject to stable selection in the presence of the neomycin analogue G418. After 21 days, the surviving colonies were stained by crystal violet and scored. In addition, some of the colonies were expanded and subject to analysis of the state of the retroviral vector DNA segments in the context of the host genome. Restriction analysis confirmed whether the DNA has integrated or is present as a episome.

These studies thus validate that transient retroviral producer cell lines can be derived with adenoviral vector-mediated delivery of retroviral packaging and vector functions. Further, transduction-competent retroviral particles can be generated, capable of achieving long term gene expression in target cells based on integration of transgene containing proviral sequences. In addition, a direct comparison of the number of functional transducing retroviral vector particles obtainable via adenoviral vector mediated-induction of a retroviral packaging line can be made in relation to standard methods.

EXAMPLE 10

Parameters for Optimal Production of Retroviral Particles Via the Adenoviral/retroviral Chimeric System Parameters which affect retroviral production from packaging cells include host cell factors, as well as the levels of retroviral packaging/vector functions achievable. In this regard, levels of adenoviral vector-mediated heterologous gene expression are generally a linear function of input particle number. This relationship holds until adenoviral vector-related toxicity attenuates heterologous gene produced by transduced cells. The determinants of optimized retroviral production via the adenoviral/retroviral chimeric system are shown. HeLa cells were co-transduced with equimolar amounts of the adenoviral vectors encoding retroviral packaging functions (AdCMVAmpg) and retroviral vector functions (AdLNCMVLacZ). As before, supernatants were harvested and analyzed for retroviral particle production. The amount of input adenoviral vector can be varied to determine its relationship to retroviral vector output. Thus, HeLa cells were infected with adenoviral vectors at multiplicities of infection of 1, 10, 100, 500, and 1,000 particles/cell. Adenovirus-mediated cytotoxicity in retroviral producer cells (HeLa) was directly determined employing the MTT assay of cellular proliferation. Based on this analysis, the relationship between input adenoviral vector and output retroviral vector as may be dictated by limiting toxicities and/or linearity of response was determined.

Another variable which may affect net output of viral particles is the ratio of retroviral packaging functions and retroviral vector sequences realized in the retroviral producer cell. This is accomplished empirically in the context of stable retroviral producer lines by determining the producer cell lines with the highest retroviral titer. The ability to independently modulate both components of the system allows determination of the optimal ratio of packaging and vector functions to allow retroviral vector production. HeLa cells were co-infected with the adenoviral vector encoding retroviral packaging functions (AdCMVAmpg) and the adenoviral vector encoding retroviral vector functions (AdLNCMVLacZ) with analysis of product retroviral particle. Linear ratios of the two particles (1:1, 1:2, 1:4, etc.) were delivered with final analysis for transducing retroviral particles. These studies allowed a determination of the precise ratios of retroviral functions most consistent with vector production in the context of the adenoviral/retroviral chimeric system.

EXAMPLE 11

Retroviral Production Via the Adenoviral/retroviral Chimeric System in Murine Cell Lines Methods to achieve cell-specific delivery with long term gene expression were examined with respect to airway epithelium (lung), vascular endothelium (heart), and liver (metabolic blood, i.e., hemophilia). The capacity of murine hepatocytes to function as retroviral producer cells was determined. For this analysis, direct comparison was made between stable retroviral vector producer cells, 293 cells transiently transfected with retroviral packaging and vector plasmids, and both HeLa cells and the murine hepatoma cells infected with equivalent amounts of the adenovirus/retrovirus vectors with packaging and vector functions. Derived retroviral particles were analyzed. This analysis shows a direct determination as to the level at which murine cells from a relevant parenchymal organ target can function as transient retroviral producer cells.

Murine cells can be infected by ecotropic and amphotropic retroviral vectors. Retroviral vectors derived from either ecotropic or amphotropic env glycoproteins were of comparable efficacy. It has not been established, however, whether murine cells function differentially with respect to production of ecotropic versus amphotropic retroviral vectors. As the methods of the present invention involve local production of retroviruses in situ in the context of murine parenchymal cells, the ability of the murine hepatocyte line to produce ecotropic versus amphotropic retroviral vectors via the adenoviral/retroviral chimeric strategy was shown.

To achieve this, a flexible approach was developed to alter the envelope glycoprotein in retroviral particles. An adenoviral vector encoding the retroviral packaging functions gag and pol (AdCMVGP) was developed. In addition, distinct adenoviral vectors encoding either the ecotropic or amphotropic env glycoprotein were developed. It is thus feasible to derive amphotropic retroviral particles by co-transductions of target cells with AdLNCMVLacZ and the adenoviral vectors encoding gag/pol (AdCMVGP) and amphotropic env (AdCMVEnv$^a$) or to derive ecotropic retroviral particle by co-transfection of target cells with AdLNCMVLacZ and the adenoviral vectors encoding gag/pol (AdCMVGP) and ecotropic env (AdCMVEnv$^e$) via the adenovirus/retrovirus chimeric system of the present invention.

For this analysis, the murine hepatocyte cell line was subjected to infection with the relevant combination of adenoviral vectors, inducing them to function either as transient producers of recombinant ecotropic or amphotropic retroviral vectors. The derived vectors were then analyzed by titer against NIH-3T3, with scoring via LacZ gene expression and neo selectable clones. This analysis determines any cellular constraints with respect to murine cells functioning as retroviral producer cells. It will also directly determine specific production issues relevant to production of ecotropic versus amphotropic retroviral vectors.

EXAMPLE 12

Retroviral Vector Production Via the Adenoviral/retroviral Chimeric System in Murine Primary Cells Murine primary cultures of hepatocytes were established employing standard methods of collagenase digestion and purification. These target cells were evaluated for a variety of parameters relevant to retroviral production including: 1)

the pattern and magnitude of retrovirus packaging function genes induced by the adenoviral/retroviral chimeric system; 2) the magnitude of production of retroviral vectors induced by the adenoviral/retroviral chimeric system; 3) the optimization of parameters for production of retroviral vectors induced by the adenoviral/retroviral vector chimeric system; 4) the differential production of ecotropic and amphotropic retroviral vectors via the adenoviral/retroviral vector chimeric system. These studies use as endpoint assays the production of transducing retroviral particles as assayed by LacZ histochemical positivity and neomycin resistance. This allows the determination of the optimal parameters relevant to retroviral vector production in the context of an appropriate target cell will the highest level of analogy to the in vivo context.

EXAMPLE 13

Retroviral Receptor Induction as a Means to Augment Retroviral Transduction via the Adenoviral/retroviral Chimeric System In situ generation of retroviral vectors that transduce neighboring parenchymal cells allowS for their stable genetic modification. Once a high local concentration of retroviral vectors has been generated via the adenoviral/retroviral chimeric approach, other factors may have a bearing on the actual transduction of surrounding target cells. In this regard, for stable genetic modification of target cells to occur via retroviral vectors, the transduced cells must be in a proliferative state. The local concentration of receptor for the produced retrovirus may also be a factor dictating the efficacy at which neighbor cells are transduced. The receptor levels for ecotropic or amphotropic viruses can be a limiting factor dictating overall susceptibility of a target cell to infection with this vector. In addition, heterologous expression of the cognate retroviral receptor can: 1) increase the susceptibility of target cells by increasing the number of effective transducing events based on receptor-env interactions and/or 2) render previously resistant cells sensitive to retroviral infection by providing the previously deficient function allowing receptor-env interaction. Modulation of retrovirus receptor population may be an important determinant of transductional efficacy with these vectors.

cDNA clones were obtained for the receptors corresponding to the envelope glycoprotein of ecotropic retrovirus (eco-R) and for the envelope glycoprotein of amphotropic retrovirus (ampho-R). These have been configured into adenoviral vectors, whereby the retroviral receptor is expressed via the CMV intermediate early promoter/enhancer in the context of an E1A/B deleted, replication-incompetent adenoviral vector. These vectors are employed to infect primary murine hepatocytes by standard procedure. These target hepatocytes are then subject to infection with ecotropic and amphotropic retroviral vectors encoding the LacZ/neo cassette. Comparison is made to murine primary hepatocytes which have not been transduced with retroviral encoded cDNAs. As before, indicator cells are scored for retroviral induction of LacZ histochemical positivity and neomycin resistance. Additional parameters which may be evaluated include the effect of target retroviral receptor number on retroviral vector sensitivity. In addition, the differential capacities of ecoR and amphoR induction can be compared. These studies determine if retroviral receptor induction can enhance retroviral transduction of relevant target cells. This strategy exploits the efficient in vivo gene transfer characteristics of adenoviral vectors to achieve the retroviral receptor induction in situ. Thus, adenoviral vectors are used to generate retroviral producer cells at target organ sites to infect neighboring cells via elaborated retroviral particles. The enhancement of this process via induction of retroviral receptors at the neighboring cells also exploits adenoviral vector mediated gene delivery.

EXAMPLE 14

Production of VSV-G Pseudotyped Retroviral Vectors Via the Adenoviral/retroviral Chimeric System Pseudotyped retroviruses have been employed to overcome target cell retroviral receptor limitations in the context of achieving efficient gene transfer via retroviral vectors. In this regard, chimeric retroviral particles may be generated which contain alternate env glycoproteins, most generally derived from vesicular stomatitis virus G-glycoprotein (VSV-G). These chimeric retroviral particles may then infect cells by virtue of the VSV-G glycoprotein's interaction with target cell receptors. This means of achieving alternate cellular entry may thus obviate the lack of target receptors for amphotropic or ecotropic env glycoproteins. This strategy has been employed both to infect retroviral resistant cells, as well as a means to increasing transduction efficiency. In addition, these pseudotyped vectors may possess a higher level of stability in vivo, potentially allowing for higher levels of in situ transduction in the in vivo delivery context. These VSV-G pseudotyped retroviruses are generated by coordinate expression of amphotropic or ecotropic gag/pol with the VSV-G glycoprotein. The assembling retroviral particle incorporates VSV-G instead of the amphotropic or ecotropic env counterpart. One means to achieve this end has been co-transduction of cells with plasmids encoding retroviral gag/pol and VSV-G plus retroviral vector plasmids. Transduced cells are rendered as transient producers of retroviral pseudotypes. Whereas this method may produce the desired pseudotyped retroviral particles, toxicity associated with the VSV-G glyoprotein is manifested in producer cells which eventuates in attenuated production and thus reduced overall titers. Packaging cell line strategies have been developed exploiting regulatable expression units. Stable cells are derived which constitutively express retroviral gag/pol and also contain VSV-G in an inducible expression cassette. Following transduction of these cells with a retroviral vector plasmid, VSV-G expression was induced to allow derivation of pseudotyped vectors. This maneuver allows the stable maintanence of cell lines capable of generating pseudotyped particles, as well as allowing an augmented level of vector production.

An adenoviral/retroviral chimeric system was employed to render target cells into transient producers of VSV-G pseudotypes. This manuever may have advantages in infecting neighbor cells in vivo. Such an augmented transduction efficiency may reflect improved target cell infection efficiencies. Alternatively, such an observation might reflect greater in vivo stability of the pseudotyped retroviral particles. For this analysis, target cells were exployed as model systems of increasing strigency. Thus, HeLa cells, the murine hepatocyte cell line BNL CL.2, and finally murine primary liver cells were induced as transient VSV-G pseudotyped retroviral producers by the adenoviral/retroviral chimeric system.

For generation of pseudotyped retroviruses, cells were co-infected with an adenoviral vector containing retroviral gag/pol, CAdCMVGP, an adenovirus encoding retroviral vector sequences (AdLNCMVLacZ), plus an adenoviral vector encoding the VSV-G glycoprotein. This latter vector was obtained from L. Prevec (McMaster University, Ontario, Canada). This is an E1A/B deleted replication-incompetent adenoviral vector capable of expressing VSV-G at high levels of various eucaryotic target cells. These cells were also induced for generation of ecotropic and amphotropic retroviral vectors via the adenoviral/retroviral chimeric system employing AdCMVEnv$^e$ and AdCMVEnv$^a$, respectively. After infection, cell supernatants were harvested and used to infect target indicated cells. Initially, NIH 3T3 cells were infected with scoring for LacZ induction and the generation of neomycin selectable clones.

This analysis gives an index of the relative titers which may be generated for VSV-G pseudotypes by this method compared to the amphotropic and ecotropic retroviral vectors. In addition, the supernatants were employed to infect murine hepatocyte primary cells with LacZ scoring. This analysis determines whether the pseudotyping maneuver allows a greater infectivity of parenchymal targets based on VSV-G target cell receptor interactions. Correlative studies determined if the VSV-G transduction event was associated with vector proviral integration. This is important as VSV-G has been associated with "pseudo-transduction" whereby heterologous gene product transfer occurs within actual stable genetic modification of the target cells. Additionally, whether induced expression of the VSV-G glycoprotein can further optimize vector production via the adenoviral/retroviral chimeric system was determined. Whether this inductibility allows higher titers VSV-G pseudotypes to the derived was evaluated. These studies thus allow determination of whether the adenoviral/retroviral chimeric system may function to yield VSV-G pseudotyped retroviral particles. Further, whether these particles possess an augmented transduction capacity for relevant parenchymal targets in vitro was determined.

EXAMPLE 15

Adeno/retro Chimeric Vectors to Modify Parenchymal Cells in Vivo

The present invention establishes methods to use adenoviral vectors to induce target cells to function as retroviral producer cells. Further, these methods can be optimized to target tissues relevant to models of heart, lung, and blood disease. Using this strategy in vivo, one may achieve long term stable integration at target parenchymal sites. In vivo studies were undertaken in two delivery contexts: 1) hepatocyte transduction via systemic vascular delivery and 2) airway epithelial transduction via lumenal airway delivery. These routing schemas represent delivery routes whereby high efficiency in vivo transduction of relevant parenchymal can be achieved. Thus, in vivo retroviral delivery efficacy of gene functions is not a confounding variable. Adenoviral vectors were employed to induce target cells to function as retroviral producers. The elaborated retroviruses then function to transduce surrounding parenchymal cells.

EXAMPLE 16

In situ Retroviral Infection of Target Cells after in Vivo Induction of Retroviral Production at Parenchymal Sites The degree and extent to which retroviruses were elaborated in vivo was determined. As the produced virions can not be feasibly retrieved after generation in situ, this analysis determines this result indirectly, by evaluating the degree to which neighbor cells have been stably transduced via retroviral vectors. For these studies, mice were challenged with a combination of the adenoviral vector encoding retroviral packaging functions and the adenoviral vector encoding retroviral vector sequences to achieve either airway epithelial or hepatocyte delivery. The expression of the packaging functions and the expressed product of the derived retroviral vector (LacZ/neo) were independently confirmed at target organs via quantitative polymerase chain reaction of mRNA transcripts (gag/pol/env) and/or DNA copy number (LTRLacZ/neo). In addition, target cells specifically producing these retroviral components were determined by in situ hybridization of tissue sections deriving from the lung and liver. These studies confirm that adenoviral vector delivery can achieve expression of retroviral packaging functions in vivo at target organ sites. Further, specific cells subset potentially functioning as retroviral producer cells can be identified.

Determination of the degree to which integration may be occurring by target cell transduction with elaborated retroviruses is carried out by analysis of the state of proviral DNA within the context of host organ genomic DNA. After local elaboration of retroviral particles, transduction of surrounding cells should generate integrated copies of the retroviral proviral genome. Total cellular DNA was extracted after induction with the adenoviral/retroviral chimeric system and subjected to analysis for the state of proviral DNA. Initially, tissue material undergoes Hirt DNA extraction. Derived DNA was then analyzed by Southern Blot for the presence and state of adenovirus-derived sequence. The majority of the retroviral vector DNA should be detected as non-integrated episomes within the Hirt fraction. This would be the case for AdCMVAmpg genomes, as well as least a portion of the AdLNCMVLacZ genomes. Next, high molecular weight DNA were analyzed in a similar manner. The genome of the two adenoviral vectors should not be detected in the HMW DNA fraction, as they are episomal, and migrate in the context of Hirt extractable DNA. In contrast, if integration occurs to any extent, the proviral component of AdLNCMVLacZ are detected in the high molecular weight fraction by Southern blot analysis. This was confirmed by restriction endonuclease digestion in combination with Southern blot of both Hirt fractions and HMW fractions of DNA derived from these two target organ sites. Comparison were made to controls whereby delivery of only retroviral packaging functions or retroviral vector functions via adenovirus was carried out. This analysis functions as a high sensitivity "screen" to determine whether an integration event has occurred as a result of in situ retroviral vector transduction via the adenoviral/retroviral chimeric system.

An additional assay of in situ retroviral infection is longevity of vector proviral DNA or DNA-encoded sequences at the target site. Stable, long term gene expression derives from in situ retroviral infection of these target organs. In the first instance, integration of the vector proviral DNA at target organ parenchymal cells would be manifested as long term persistence of this DNA sequence in the context of the host genome DNA. Thus, the temporal pattern of the vector proviral DNA was examined. In this regard, animals were challenged, as before, with the combination of AdCMVAmpg and AdLNCMVLacZ for lung and liver transduction. At specific time intervals post-treatment, the indicated organs are harvested and subject to both Hirt DNA extractions and HMW DNA extractions. Analysis of the amount of both adenoviral vector genomic DNA and retroviral proviral DNA was undertaken by employing quantitative PCR to determine absolute amounts of the integrated retroviral vector DNA within host HMW genomic DNA at each time point. A temporal profile indicating persistence proviral vector sequences within the HMW fraction indicates the degree to which stable integration has occurred. An additional index of persistence, based on vector proviral integration, was carried out employing histochemical reporters. Both LacZ and GFP were employed as reporters whose expression can be deleted by histochemical analysis of appropriate processed tissue section. The transient expression profile of these reporter genes at the airway epithelium and liver after adenoviral vector transduction has been well documented. Thus, the temporal pattern of the reporter gene should be indicative of in situ retroviral generation with consequent integration of vector proviral DNA. Animals were challenged with AdCMVAmpg and AdLNCMVLacZ, or AdLNCMVGFP, for liver and lung transduction. At various time points post-treatment, relevant organs were harvested with histochemical analysis for the products of the encoded LacZ and GFP genes. This analysis was complemented by in situ hybridization of tissue sections for the mRNA production of these reporter genes to provide an additional quantitative index. In this analysis, a differential in the pattern of persistence would be anticipated in the in situ retroviral vector group compared to reporter encoding adenoviruses alone.

EXAMPLE 17

Enhancement of in Situ Retroviral Infection Via in Vivo Adenoviral Delivery of Retroviral Packaging and Vector Functions The ability of locally elaborated retroviral vectors to stably transduce parenchymal target cells is impacted by local cellular factors. These factors include the proliferative state of the target cell as well as the number of receptors for the locally produced retroviral vectors. To modulate target cell proliferation, a strategy based on growth factor induction was used. A strategy of growth factor induction for enhancement of target cell proliferation was used; however, adenoviral vectors were employed to achieve efficient in vivo delivery to the lung and liver of a gene construct encoding the growth factors KGF and hepatocyte growth factor (HGF). High local concentrations of these growth factors achieved by this method provide an optimized induction of proliferation of parenchymal cells at these organ sites and this proliferation induction allows enhanced transduction of target cells by locally elaborated retroviral vectors.

Animals were initially challenged by delivery of adenoviral vectors encoding KGF or HGF to the lung or liver. After establishment of the temporal profile for optimal induction of proliferation, animals were challenged with the adenoviral/retroviral chimeric vectors AdCMVAmpg and AdLNCMVLacZ for in situ retroviral generation. These animals then underwent analysis to determine the degree of integrated proviral vector sequences. These studies include PCR quantification of integrated proviral sequences within the HMW DNA fraction of lung and liver, as well as in situ hybridization for determination of the number of stably transduced cells. Correlative studies determine the degree to which induced proliferation was a factor predicting successful in situ retroviral transduction. The aggregate of these studies allows the determination of the degree to which induced proliferation via adenoviral vector-mediated delivery of growth factor genes can favorably influence the ability of in situ generated retroviral vectors to achieve stable transduction of parenchymal targets.

EXAMPLE 18

Adenoviral Vectors can Induce Target Cells to Function as Retroviral Producers

Target cells were infected with a combination of the adenoviral vectors, AdCMVAmpg and AdLNCMVGFP, or with AdLNCMVGFP only. Target cells were either the monkey vero cell line WI62, the murine fibroblast cell line NIH-3T3, the human bladder cancer cell line EJ, or the human ovarian cancer cell line SKOV3$_{ip1}$ (data not shown). Cells were infected with the appropriate adenoviral vectors for 3 h and then washed to remove any free adenovirus. These cells were maintained in tissue culture for various time periods and then analyzed for the expression of the green fluorescent protein (GFP) reporter gene by fluorescence-activated cell sorting (FACS) or by fluorescent microscopy.

Figure 5:
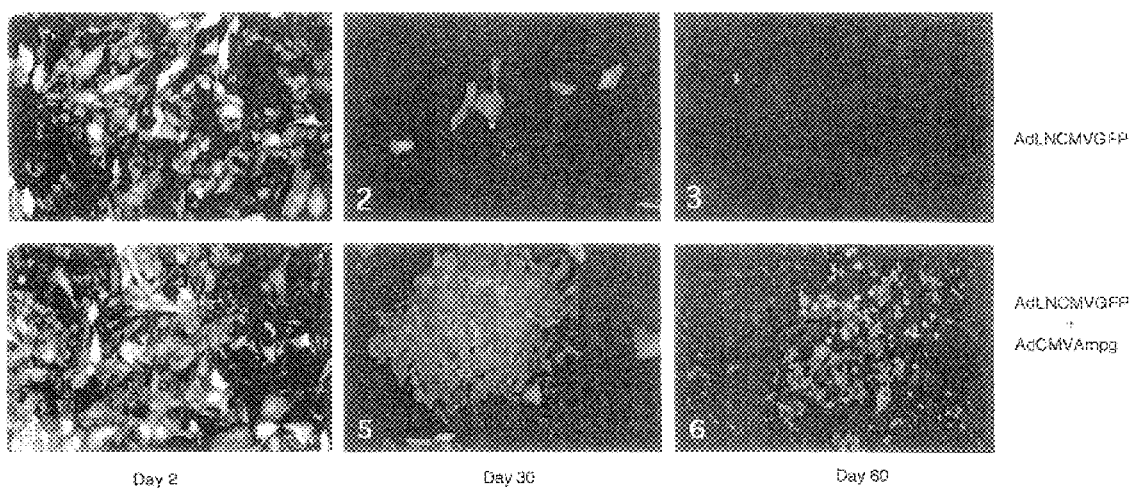
FIG. 5 (Parts A–F) shows the persistant gene expression achieved via the adenoviral/retroviral chimeric vector system. Target cells were infected with AdLNCMVGFP plus AdCMVAmpg or AdLNCMVGFP alone and then analyzed for stable genetic transduction. GFP expression in W162 cells was analyzed by fluorescent microscopy at indicated time points after adenoviral vector infection.
Figure 6A:
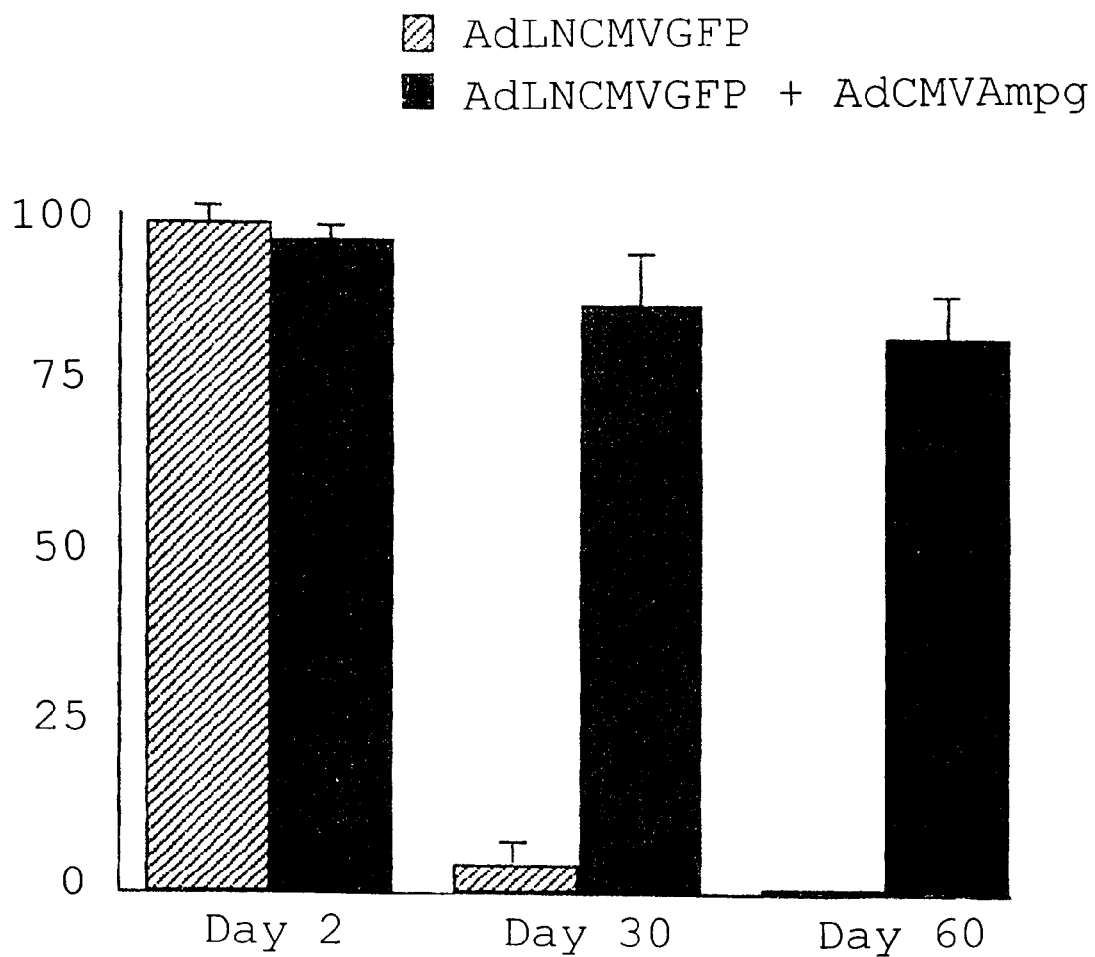
FIG. 6A shows the FACS analysis of GFP expression in W162 cells at indicated times post-infection.
Figure 6B:
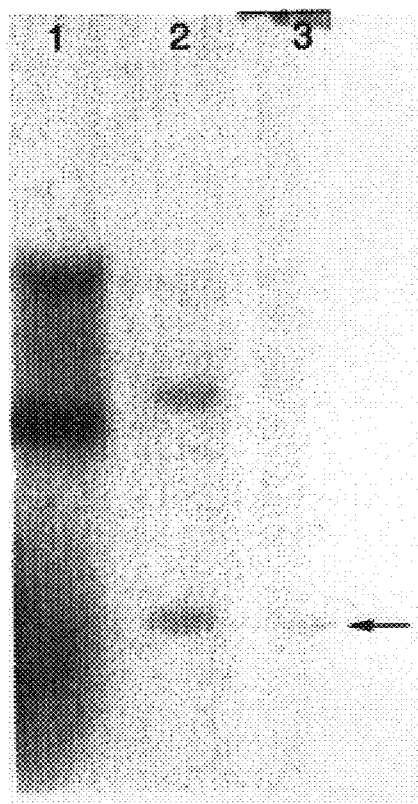
FIG. 6B shows an analysis of genomic DNA extracted from W162 cells harvested at day 30 post-infection. HMW DNA of cells was digested with MunI, and probed with a retrovirus vector-proviral segment. The DNA in lane 1 was extracted from cells infected with AdLNCMVGFP and AdCMVAmpg; lane 2 DNA was extracted from cells infected with AdLNCMVGFP alone; and lane 3 is a control containing AdLNCMVGFP genomic DNA digested with MunI.

Analysis of adenoviral vector infected cells at day 2 post-infection showed that both groups, the control and the putative retroviral producers, demonstrated a high frequency of expression of the GFP reporter gene (FIG. 5). This is consistent with a high initial frequency of AdLNCMVGFP infection having occurred in both groups, with subsequent GFP gene expression occurring in both groups as well. A subset of each group was passaged every 8 days and then analyzed at day 30 and day 60. FACS analysis of the cell group that had been exposed to both adenoviral vectors (AdCMVAmpg and AdLNCMVGFP) showed a substantially higher number of GFP-positive cells compared with the cells that had received only AdLNCMVGFP (FIG. 6A). The GFP-positive cells from the group infected with both viruses were present in clustered out-growths suggesting local retroviral spreading and/or clonal origin (FIG. 5). This is in marked contrast to the cells infected with AdLNCMVGFP alone, which had lost GFP expression, consistent with the known transient expression of genes delivered by the standard adenovirus approach (FIGS. 5 and 6A). Proviral integration was confirmed by the demonstration of retroviral sequences in high-molecular-weight cellular DNA (FIG. 6B).

EXAMPLE 19

Production of Transducing Retroviral Particles

Figure 7:
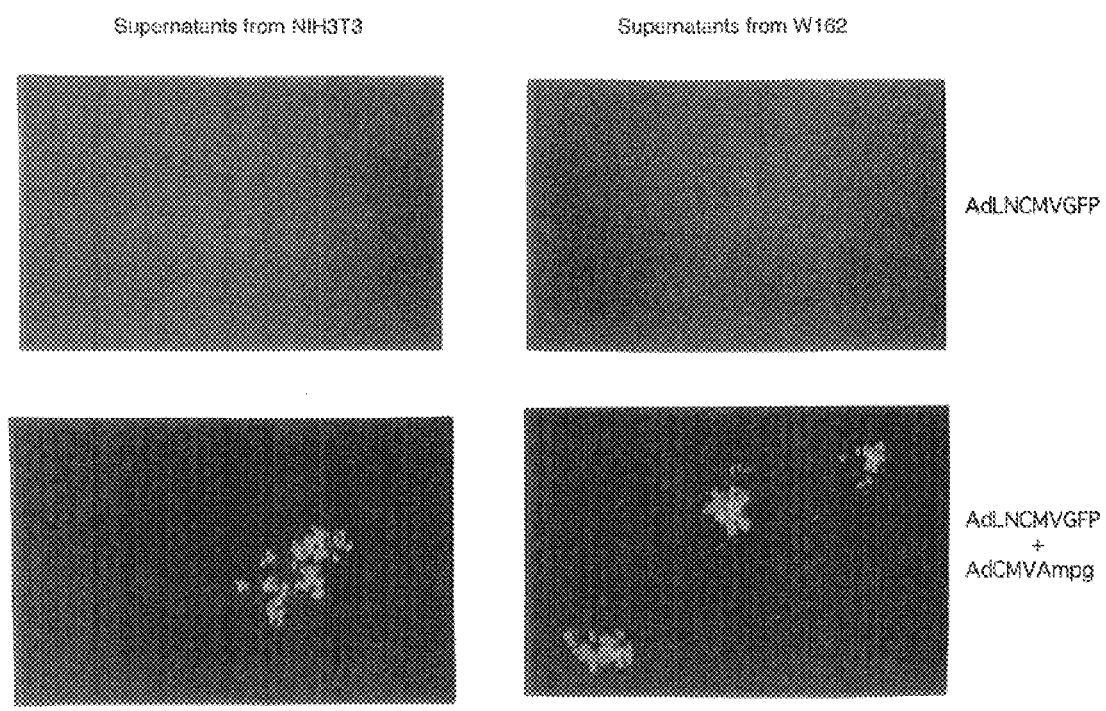
FIG. 7 shows the derivation of transducing retroviral particles via the adenoviral/retroviral chimeric vector. Indicated cells were treated with AdLNCMVGFP only or AdLNCMVGFP plus AdCMVAmpg and supernatants analyzed for retroviral vector particles by titering on NIH-3T3 cells. Supernatant treated cells were analyzed at day 20 by fluorescent microscopy.

NIH-3T3 or WI62 cells were infected with either a combination of AdCMVAmpg and AdLNCMVGFP, or AdLNCMVGFP only, then subsequently washed as before. The supernatants were harvested at 48 h postinfection and then used to infect NIH-3T3 cells to determine retroviral titers. The supernatant-infected cells were maintained in culture for 20 days and analyzed for GFP expression. The supernatant derived from the AdLNCMVGFP-virus infected cells was not capable of inducing long-term GFP expression in target cells (FIG. 7). In contrast, cells infected with AdCMVAmpg plus AdLNCMVGFP supernatant demonstrated a high rate of GFP expression at day 20. This study confirms that GFP induction resulted from infection with retroviruses derived from the original adenovirus-infected target cells. These long-term GFP expression studies were designed to distinguish carryover adenoviral transient gene expression (<2 weeks) from stable transduction mediated by retrovirus production. The results suggested that transducing retroviral particles had indeed been generated by adenoviral-vector delivered genes in target cells.

To determine whether this methodology was associated with significant production of replication-competent retrovirus (RCR), RCR generation derived via plasmid-based transfection methods was compared to the use of the adenoviral/retroviral chimeric vector. HeLa cells were thus transfected with either pPAM3 plus pLNCLZ, or infected with AdCMVAmpg or AdLNCMVGFP, or AdCMVAmpg plus AdLNCMVGFP. These supernatants were then analyzed for the presence of replication-competent retroviruses.

No replication-competent retroviruses were detected with the adenoviral/retroviral chimera (data not shown). Thus, the generation of replication-competent retroviruses by this method does not appear to be in excess of conventional methods.

EXAMPLE 20

In Vivo Gene Transfer with Stable Integration

Figure 8A:
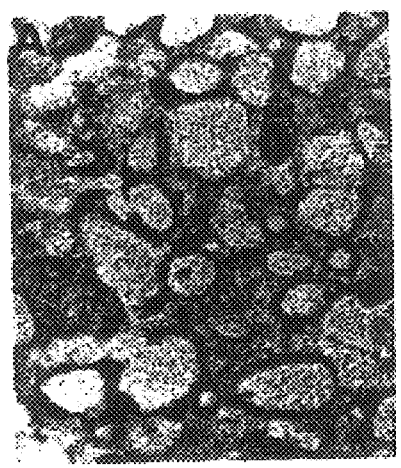
FIG. 8A shows a hematoxylin stained intraperitoneal tumor nodule. Animals challenged with either FIG. 8B AdLNCMVGFP alone or (FIG. 8C) AdLNCMVGFP and AdCMVAmgp were analyzed by fluorescent microscopy for expression of GFP at day sixteen.
Figure 8B:
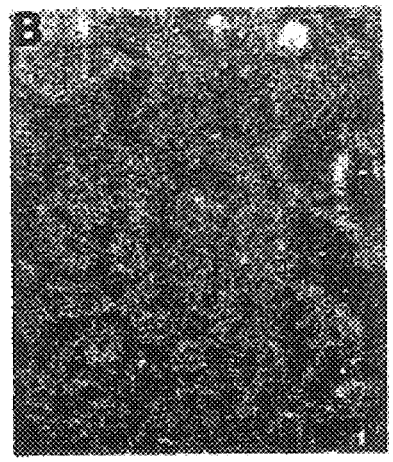
FIG. 8 shows in vivo gene transfer via the adenoviral/retroviral chimeric vector. SKOV3$_{ip1}$ cells were implanted intraperitoneally.
Figure 8C:

Having established these key concepts, this methodology was employed to accomplish in vivo gene transfer with stable integration. This was carried out to determine the overall utility of this approach in the most stringent delivery context. For this analysis, a murine model of human carcinoma of the ovary was employed. Athymic nude mice were thus xenografted orthotopically with the human carcinoma cell line $SKOV3_{ip1}$. After establishment of peritoneal tumor plaques, animals were then vector challenged via the intraperitoneal (i.p.) route. Groups of animals received either the adenoviral/rectroviral vector chimeric or this vector plus the adenoviral/retroviral packaging chimera. In the former instance, the employed vector, AdLNCMVGFP, contained retroviral vector sequences with the GFP reporter gene. In the latter instance, the adenoviral vectors AdCMVAmpg, derived from pCAAmpg, contained the functionally validated retroviral packaging functions. In the one virus group, the adenoviral vector-mediated delivery of the GFP expressing cassette should result in in vivo gene expression with a temporal profile of rapid extinction based on non-integrative heterologous gene transfer. In contrast, the two viruses were anticipated to achieve in situ induction of tumor cells to function as retroviral producer cells. The locally elaborated retroviral vectors would then be anticipated to achieve stable transduction of proliferative neighbor cells, in this instance, the $SKOV3_{ip.1}$ carcinoma targets. Based upon these considerations, the two original groups would be anticipated to exhibit distinctly different temporal profiles of expression of the GFP reporter gene based on their differential ability to acheive stable transduction. Animals treated with the adenoviral/retroviral vector chimera AdLNCMVGFP were analyzed by fluorescent microscopy for tumor cells exhibiting GFP expression at early and late points post-delivery. In this analysis, the group of animals receiving the single vector demonstrated rare single positive cell at late time points as shown in FIG. 8. In contrast, the animals that received the combination of adenoviral/retroviral vector chimera plus the adenoviral/retroviral packaging chimera exhibited a distinctly different pattern at late time points. In this regard, the analysis of this group was noteworthy for the detection of increased numbers of positive cells which occurred in clusters. This finding was consistent with the concept that stable transduction of target cells had occurred with clonal expression.

EXAMPLE 21

In Vivo Efficacy of the Adenoviral/retroviral Chimera

Figure 9A:
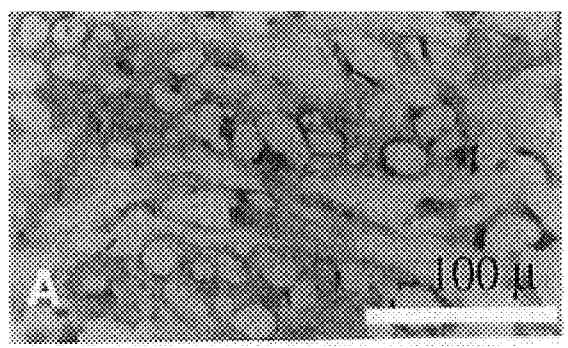
FIG. 9 (Parts A–F) shows in vivo gene transfer via the adenoviral/retroviral chimeric vector. SKOV3$_{ip1}$ cells were infected with either AdLNCMVGFP (FIG. 9B) or AdLNCMVGFP plus AdCMVAmpg (FIG. 9C), mixed with virgin tumor cells and implanted subcutaneously in athymic nude mice. At day 20, tumors were harvested and analyzed by fluorescent microscopy.
(FIG. 9D) A hematoxylin stained intraperitoneal tumor nodule.
Figure 9B:
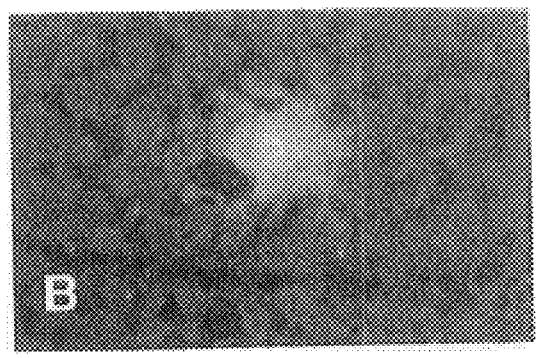
Figure 9C:
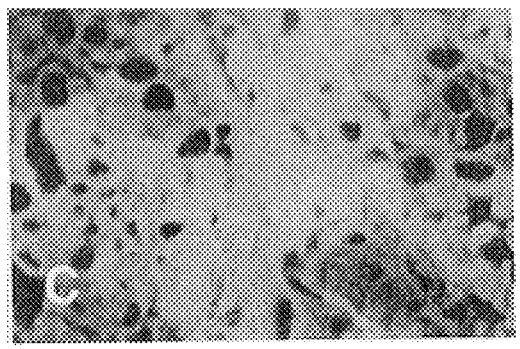
Figure 9D:
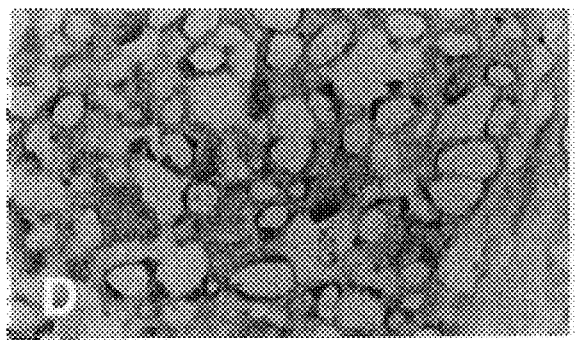

The ovarian carcinoma cell line $SKOV3_{ip1}$ was infected in vitro with either AdCMVAmpg plus AdLNCMVGFP, or AdLNCMVGFP alone. To confirm the in vivo generation of infected retroviral particles and infection of neighboring cells, infected cells were mixed with uninfected cells at a ratio of 25% adenoviral-vector infected cells with 75% untreated $SKOV3_{ip1}$ cells and implanted subcutaneously in athymic nude mice to allow tumor formation. Twenty days after implantation, both animal groups had palpable tumors that were harvested for analysis of GFP reporter gene persistence and expression. The group infected with AdLNCMVGFP only had rare, isolated fluorescent cells (FIG. 9B). In contrast, the tumors derived fom the two-virus group had large expansive clusters of GFP positive cells (FIG. 9C). Counting of positive cells in multiple fields allowed an estimate of transduced cells such that the one-virus group had >80% GFP-positive cells. Thus, in this group, the number of positive cells was substantially greater than the proportion of adenovirally infected cells in the original implanted mixture. The extensive distribution of GFP-positive cells in the two-virus group suggested stable genetic modification of neighboring cells via in situ retroviral vectors.

Figure 9E:
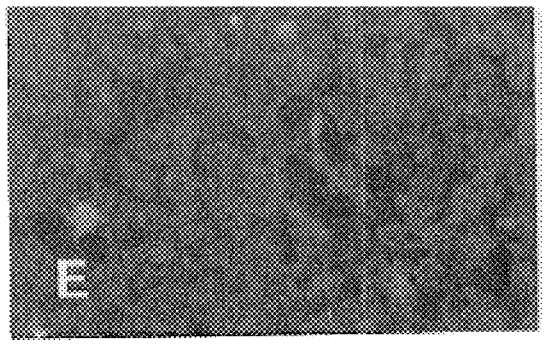
Figure 9F:
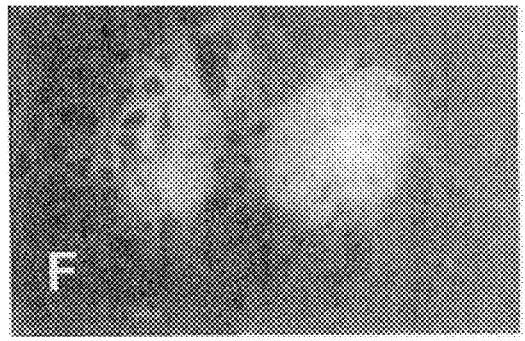

The potenital to link in vivo adenoviral vector transduction to in situ retroviral producer generation was examined. Nude mice were orthotopically transplanted with the human ovarian cancer cell line $SKOV3_{ip1}$. Five days post-implantation, animals were treated intraperitoneally with either AdLNCMVGFP only, or AdLNCMVGFP plus AdCMVAmpg. 16 days post-adenovirus infection, the animals were sacrificed and tumors analyzed. No GFP-positive cells could be detected in the one-virus group (FIG. 9E). In contrast, islands of GFP-positive cells could readily be detected in the group that received both adenoviral vectors (FIG. 9F). Again, analysis of multiple microscopic fields demonstrated an overall transduction rate of <1% for the one-virus group and 10–15% for the two-virus group. The persistance of GFP expression in vivo in the group receiving the two adenoviral vectors, which allow full induction of retroviral packaging, is consistent with the in vitro findings whereby stable transduction had occurred based on secondarily elaborated retroviral vectors.

EXAMPLE 22

Summary

A novel vector approach has been developed to achieve efficient and stable genetic modification of target cells in vivo. This was accomplished by using the adenovirus as a delivery system for retroviral vector and packaging components and therefore inducing target cells to function as transient producers of retroviral vectors in situ. This strategy thus allowed the generation of retroviral vector particles capable of infecting neighboring cells and accomplishing stable transduction. In this approach, two key factors allowed this level of stable transduction in vivo. First, the local production of retroviral vectors at the site of the target cells circumvented the deleterious effects of exposure of the retroviral particles to humoral factors which would have resulted in their inactivation. Second, the efficient induction of retroviral producer cells in situ capitalized on the ability of adenoviral vectors to achieve effective in vivo delivery to target cells. This strategy thus represents a novel conceptual approach whereby desirable aspects of component vector systems are combined to achieve a gene delivery goal.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed:

1. A chimeric adenoviral/retroviral vector composition, wherein said chimeric adenoviral/retroviral vector composition comprises:
   (a) a replication-deficient adenoviral vector containing retroviral vector functions; and
   (b) at least one replication-deficient adenoviral vector containing retroviral packaging functions.

2. The vector composition of claim 1, wherein said retroviral vector functions comprise a heterologous gene flanked by retroviral long terminal repeats.

3. The vector composition of claim 1, wherein said retroviral packaging functions are selected from the group consisting of gag, pol and env, or combinations thereof.

4. The vector composition of claim 2, wherein said heterologous gene is selected from the group consisting of a gene encoding a therapeutic protein, a selectible marker and a reporter gene.

5. The vector composition of claim 3, wherein said env gene encodes a vesicular stomatitis virus G-glycoprotein.

6. A method of stably transducing target cells, comprising the step of:
co-transducing said target cells with a chimeric adenoviral/retroviral vector composition, said composition comprising:
   (a) a replication-deficient adenoviral vector containing retroviral vector functions; and
   (b) a replication-deficient adenoviral vector containing retroviral packaging functions, wherein expression of the genes encoded by said adenoviral vectors results in the production of retrovirus particles that would infect neighboring cells and stably integrate into said cells' genomic DNA.

7. The method of claim 6, wherein said retroviral vector functions comprise a heterologous gene flanked by retroviral long terminal repeats.

8. The method of claim 6, wherein said retroviral packaging functions are selected from the group consisting of gag, pol and env or combination thereof.

9. The method of claim 7, wherein said heterologous gene is selected from the group consisting of a gene encoding a therapeutic protein, a selectible marker, and a reporter gene.

10. The method of claim 8, wherein said env gene is a vesicular stomatitis virus G-glycoprotein.

* * * * *